United States Patent
Lee et al.

(10) Patent No.: US 12,221,639 B2
(45) Date of Patent: Feb. 11, 2025

(54) ALLULOSE EPIMERASE VARIANT WITH EXCELLENT THERMAL STABILITY, PREPARATION METHOD THEREFOR, AND PREPARATION METHOD FOR ALLULOSE USING SAME

(71) Applicant: DAESANG CORPORATION, Seoul (KR)

(72) Inventors: Ji Ha Lee, Icheon-si (KR); Tae Gyun Kim, Icheon-si (KR); Baek Joong Kim, Icheon-si (KR); Da Han Jung, Icheon-si (KR); Seung Woo Cho, Icheon-si (KR); Hak Jun Kim, Icheon-si (KR)

(73) Assignee: DAESANG CORPORATION, Seoul (KR)

( * ) Notice: Subject to any disclaimer, the term of this patent is extended or adjusted under 35 U.S.C. 154(b) by 0 days.

(21) Appl. No.: 18/267,874

(22) PCT Filed: Nov. 22, 2021

(86) PCT No.: PCT/KR2021/017155
§ 371 (c)(1),
(2) Date: Jun. 16, 2023

(87) PCT Pub. No.: WO2023/090495
PCT Pub. Date: May 25, 2023

(65) Prior Publication Data
US 2024/0052389 A1    Feb. 15, 2024

(30) Foreign Application Priority Data

Nov. 19, 2021    (KR) .................. 10-2021-0160438

(51) Int. Cl.
*C12N 9/90* (2006.01)
*C07K 14/195* (2006.01)
(Continued)

(52) U.S. Cl.
CPC ............... *C12P 19/02* (2013.01); *C12N 9/90* (2013.01); *C12Y 501/03* (2013.01)

(58) Field of Classification Search
CPC ........ C12N 19/02; C12N 15/77; C12N 15/75; C12N 9/90; C12N 15/09; C12P 19/24; C07K 14/195; C12Y 501/03
See application file for complete search history.

(56) References Cited

FOREIGN PATENT DOCUMENTS

| KR | 10-1203856 B1 | 11/2012 |
|---|---|---|
| KR | 10-2014-0021974 A | 2/2014 |

(Continued)

OTHER PUBLICATIONS

Notice of Allowance issued Jun. 12, 2024 for KR 10-2021-0160438.
(Continued)

*Primary Examiner* — Maryam Monshipouri
(74) *Attorney, Agent, or Firm* — Sughrue Mion, PLLC

(57) ABSTRACT

The present invention provides a novel allulose epimerase variant in which an amino acid residue present at a specific position of an amino acid sequence of wild-type D-allulose 3-epimerase derived from *Flavonifractor plautii* is substituted with another amino acid residue, and various uses thereof. The novel allulose epimerase variant according to the present invention has a higher conversion activity of fructose to allulose than that of the wild-type D-allulose 3-epimerase derived from *Flavonifractor plautii* or a D-allulose epimerase variant W29K/G216S/M234I, and has excellent thermal stability especially under high temperature conditions of 60° C. or higher, thereby preventing contamination during an industrial-scale enzymatic conversion reaction for the mass production of allulose, shortening the production time, and reducing the production costs.

12 Claims, 1 Drawing Sheet
Specification includes a Sequence Listing.

(51) Int. Cl.
    *C12N 15/09*     (2006.01)
    *C12N 15/75*     (2006.01)
    *C12N 15/77*     (2006.01)
    *C12P 19/02*     (2006.01)
    *C12P 19/24*     (2006.01)

(56) References Cited

FOREIGN PATENT DOCUMENTS

| KR | 10-1473918 B1 | 12/2014 |
| KR | 10-2016-0050569 A | 5/2016 |
| KR | 10-2018-0055736 A | 5/2018 |
| KR | 10-2018-0132408 A | 12/2018 |
| KR | 10-2254411 B1 | 5/2021 |
| KR | 10-2021-0132405 A | 11/2021 |

OTHER PUBLICATIONS

Chul-Soon Park et al., "D-Allulose Production from D-Fructose by Permeabilized Recombinant Cells of Corynebacterium glutamicum Cells Expressing D-Allulose 3-Epimerase Flavonifractor plautii", , PLOS ONE, Jul. 28, 2016, 22 page(s), vol. 11, No. 7.

Satya Narayan Patel et al., "A Novel D-Allulose 3-Epimerase Gene from the Metagenome of a Thermal Aquatic Habitat and D-Allulose Production by Bacillus subtilis Whole-Cell Catalysis", American Society for Microbiology, Applied and Environmental Microbiology, Feb. 18, 2020, pp. 1-14, vol. 86, No. 5.

International Search Report for PCT/KR2021/017155 dated Aug. 8, 2022.

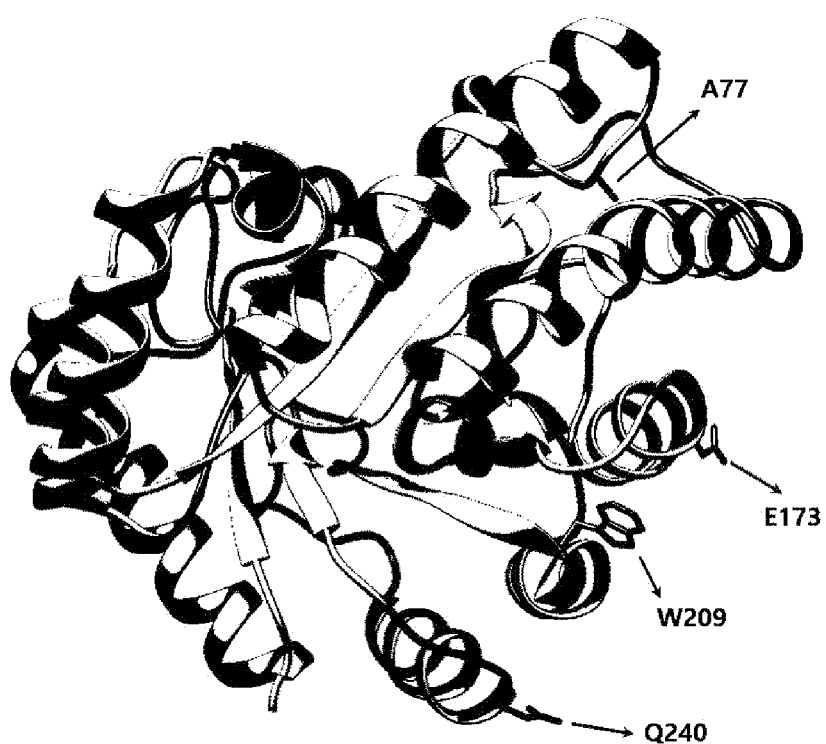

ALLULOSE EPIMERASE VARIANT WITH EXCELLENT THERMAL STABILITY, PREPARATION METHOD THEREFOR, AND PREPARATION METHOD FOR ALLULOSE USING SAME

CROSS REFERENCE TO RELATED APPLICATIONS

This application is a National Stage of International Application No. PCT/KR2021/017155 filed Nov. 22, 2021, claiming priority based on Korean Patent Application No. 10-2021-0160438 filed Nov. 19, 2021, the entire disclosures of which are incorporated herein by reference.

INCORPORATION BY REFERENCE OF SEQUENCE LISTING

The content of the electronically submitted sequence listing, file name: Q287753_sequence listing as filed.TXT; size: (26,216 bytes; and date of creation: Jun. 15, 2023, filed herewith, is incorporated herein by reference in its entirety.

TECHNICAL FIELD

The present invention relates to an allulose epimerase variant and the like, and more particularly, to an allulose epimerase variant with an improved conversion rate of fructose to allulose and thermal stability compared to D-allulose 3-epimerase derived from *Flavonifractor plautii* and various inventions derived therefrom.

BACKGROUND ART

D-allulose is also called D-psicose as an epimer of carbon 3 of fructose. D-allulose is a functional monosaccharide that has 70% sweetness compared to sugar (Oshima 2006) but only 0.3% energy to be applicable as a low-calorie sweetener in diet foods (Matsuo et al. 2002). In addition, D-allulose has a function of suppressing glucose absorption and blood sugar and can be applied to food and drink for diabetic patients, food and drink for reception, and the like, and may suppress the accumulation of abdominal fat through inhibition of enzyme activity involved in lipid synthesis in the liver and thus can be used for various functional foods such as health foods (Matsuo et al. 2001; Iida et al. 2008; Hayashi et al. 2010; Hossain et al. 2011).

With the above characteristics, allulose is a good source capable of substituting sugar, but belongs to rare sugar, which is monosaccharide that rarely exists in nature, and thus a method of efficiently producing allulose is required to apply allulose to the food industry. In existing methods for producing allulose, allulose was mainly produced through chemical processes. Bilik et al. proposed a method of converting fructose to allulose using a catalytic action of molybdate ions. McDonald produced allulose from 1,2:4,5-di-δ-isopropylidene-beta-D-fructopyranose through a three-step chemical treatment process. Also, Doner produced allulose by heating fructose with ethanol and trimethylamine. However, these chemical production methods have a disadvantage of high cost, low efficiency, and generation of a significant amount of by-products.

As a biological method for producing allulose, there was proposed a method for producing allulose from galactitol, D-tagatose, D-tallitol, or the like using a cell reaction of microorganisms (Ken Izumori). However, this method is hardly applied to industrial production because a matrix belongs to rare sugar. The most efficient method for industrialization is a method of finding an enzyme that converts fructose to allulose in a D-ketose 3-epimerase group. In previously reported contents, allulose was produced from fructose by inserting and transforming D-tagatose 3-epimerase derived from *Clostridium cellulolyticum* H (10) (Mu et al. 2011), *Agrobacterium tumefaciens* (Kim et al. 2006), *Pseudomonas cichorii* (Itoh at al. 1994), and *Rhizobium sphaeroides* (Zhang et al. 2009) into *E. coli* and then using the D-tagatose 3-epimerase expressed in the transformed *E. coli*.

Regarding a technology for producing allulose from fructose using enzymes, in Korean Patent Registration No. 10-0744479, there is disclosed a method for producing allulose using allulose epimerase derived from *Agrobacterium tumefaciens*. In Korean Patent Registration No. 10-0832339, there are disclosed the genus *Sinorhizobium* YB-58 KCTC 10983BP having an activity of converting fructose to allulose and a method for converting fructose to allulose using the same. In Korean Patent Registration No. 10-1106253, there are disclosed *Escherichia coli* including a polynucleotide encoding allulose 3-epimerase of *Agrobacterium tumefaciens* C58 having an activity of catalyzing the conversion of fructose to allulose and a method for producing allulose from fructose using the same. In Korean Patent Registration No. 10-1339443, there are disclosed ketose 3-epimerase derived from a microorganism belonging to the genus *Rhizobium* and a method for converting fructose to allulose using the same. In Korean Patent Registration No. 10-1318422, there are disclosed D-allulose 3-epimerase derived from *Clostridium scindens* and a method for producing allulose from fructose using the same. In Korean Patent Registration No. 10-1473918, there are disclosed D-allulose 3-epimerase derived from *Flavonifractor plautii* and a method for producing allulose from fructose using the same.

However, wild-type D-allulose 3-epimerase derived from microorganisms does not have a high conversion rate of fructose to allulose and has low thermal stability, and thus, is rapidly deactivated at an optimum activation temperature, making it unsuitable for industrialization. Accordingly, it is necessary to develop a novel D-allulose 3-epimerase variant with an improved conversion rate of fructose to allulose or thermal stability compared to wild type D-allulose 3-epimerase derived from microorganisms. Regarding the D-allulose 3-epimerase variant, in Korean Patent Publication No. 10-2014-0021974, there is disclosed D-allulose 3-epimerase derived from *Treponema primitia* ZAS-1 showing a fast allulose conversion rate and stability at a high temperature by inducing mutations at a gene level. In Korean Patent Registration No. 10-1203856, there is disclosed an allulose epimerase variant with improved thermal stability obtained through mutation of wild-type allulose epimerase derived from *Agrobacterium tumefaciens*. In addition, in Korean Patent Registration No. 10-2254411, there is disclosed a novel allulose epimerase variant in which glycine (Gly), which is an amino acid residue present at position 216 of the amino acid sequence of wild-type D-allulose 3-epimerase derived from *Flavonifractor plautii*, is substituted with serine (Ser). In Korean Patent Publication No. 10-2021-0132405, there is disclosed a novel allulose epimerase variant in which tryptophan (Trp) present at position 29 is substituted with lysine (Lys), glycine (Gly) present at position 216 is substituted with serine (Ser), and simultaneously methionine (Met) present at position 234 is substituted with isoleucine (Ile) in an amino acid sequence of wild-type D-allulose 3-epimerase derived from *Flavonifractor plautii*.

DISCLOSURE

Technical Problem

The present invention has been derived under the background of the prior art, and a first object of the present invention is to provide a novel D-allulose 3-epimerase variant with an improved conversion rate of fructose to allulose and thermal stability compared to wild-type D-allulose 3-epimerase derived from *Flavonifractor plautii*.

A second object of the present invention is to provide a method for producing a novel D-allulose 3-epimerase variant or various elements necessary for producing the novel D-allulose 3-epimerase variant.

A third object of the present invention is to provide a method for producing allulose from fructose or various elements necessary for producing allulose from fructose.

Technical Solution

The present applicants have filed and registered a novel allulose epimerase variant in which glycine (Gly), which is an amino acid residue present at position 216 of the amino acid sequence of wild-type D-allulose 3-epimerase derived from *Flavonifractor plautii*, is substituted with serine (Ser) [Korean Patent Registration No. 10-2254411 (May 14, 2021)]. The present applicants have filed a novel allulose epimerase variant in which tryptophan (Trp) present at position 29 is substituted with lysine (Lys), glycine (Gly) present at position 216 is substituted with serine (Ser), and simultaneously methionine (Met) present at position 234 is substituted with isoleucine (Ile) in an amino acid sequence of wild-type D-allulose 3-epimerase derived from *Flavonifractor plautii* [Korean Patent Publication No. 10-2021-0132405 (Nov. 4, 2021)]. The allulose epimerase variants disclosed in Korean Patent Registration No. 10-2254411 and Korean Patent Publication No. 10-2021-0132405 have improved thermal stability compared to the wild-type D-allulose 3-epimerase derived from *Flavonifractor plautii*, but have a decreased enzyme activity when the conversion reaction of fructose to allulose is performed for a long time at a high temperature of 60° C. or higher, and still need to be improved in terms of industrialization for mass production of allulose. The present inventors further derived amino acid residue position candidates expected to be related to improved conversion rate and thermal stability using a protein structure prediction technology in order to improve the conversion rate of fructose to allulose and thermal stability of the allulose epimerase variant disclosed in Korean Patent Publication No. 10-2021-0132405, confirmed that the conversion rate of fructose to allulose and thermal stability were improved only when an amino acid residue at a specific position among them was substituted with another amino acid residue, and then completed the present invention.

In order to solve the first object, the present invention provides an allulose epimerase variant consisting of an amino acid sequence represented by SEQ ID NO: 5.

In order to solve the second object, the present invention provides a polynucleotide encoding an allulose epimerase variant consisting of an amino acid sequence represented by SEQ ID NO: 5. In addition, the present invention provides a recombinant vector including a polynucleotide encoding an allulose epimerase variant consisting of an amino acid sequence represented by SEQ ID NO: 5. In addition, the present invention provides a recombinant strain transformed by a polynucleotide encoding an allulose epimerase variant consisting of an amino acid sequence represented by SEQ ID NO: 5 or a recombinant vector including the polynucleotide. In addition, the present invention provides a method for producing an allulose epimerase variant including expressing an allulose epimerase variant by culturing a recombinant strain transformed by a polynucleotide encoding an allulose epimerase variant consisting of an amino acid sequence represented by SEQ ID NO: 5 or a recombinant vector including the polynucleotide; and isolating the allulose epimerase variant from a lysate of the recombinant strain in which the allulose epimerase variant is expressed.

In order to solve the third object, the present invention provides a composition for producing allulose including an allulose epimerase variant consisting of an amino acid sequence represented by SEQ ID NO: 5. In addition, the present invention provides a composition for producing allulose including a recombinant strain transformed by a polynucleotide encoding an allulose epimerase variant consisting of an amino acid sequence represented by SEQ ID NO: 5 or a recombinant vector including the polynucleotide, a culture of the recombinant strain or a lysate of the recombinant strain. In addition, the present invention provides a method for producing allulose including reacting fructose with an allulose epimerase variant consisting of an amino acid sequence represented by SEQ ID NO: 5 or a composition including the allulose epimerase variant. In addition, the present invention provides a method for producing allulose including reacting fructose with a recombinant strain transformed by a polynucleotide encoding an allulose epimerase variant consisting of an amino acid sequence represented by SEQ ID NO: 5 or a recombinant vector including the polynucleotide, a culture of the recombinant strain, a lysate of the recombinant strain, or a composition including at least one thereof.

Advantageous Effects

According to the present invention, the novel allulose epimerase variant has a higher conversion activity of fructose to allulose than that of wild-type D-allulose 3-epimerase derived from *Flavonifractor plautii* or a D-allulose epimerase variant W29K/G216S/M234I, and has excellent thermal stability especially under high temperature conditions of 60° C. or higher, thereby preventing contamination during an industrial-scale enzymatic conversion reaction for the mass production of allulose, shortening the production time, and reducing the production costs.

DESCRIPTION OF DRAWINGS

FIG. 1 shows a total of four amino acid residue positions selected as substitution candidates to improve a conversion rate of fructose to allulose and thermal stability of a D-allulose epimerase variant W29K/G216S/M234I by the present inventors.

DETAILED DESCRIPTION OF EMBODIMENT

Hereinafter, the present invention will be described in detail.

One aspect of the present invention relates to a novel D-allulose 3-epimerase variant capable of converting fructose to allulose (hereinafter referred to as an 'allulose epimerase variant'). In an allulose epimerase variant W29K/A77S/G216S/M234I according to an embodiment of the present invention, in an amino acid sequence (SEQ ID NO: 1) of wild-type D-allulose 3-epimerase derived from *Fla*-

*vonifractor plautii*, tryptophan (Trp) present at position 29 is substituted with lysine (Lys), alanine (Als) present at position 77 is substituted with serine (Ser), glycine (Gly) present at position 216 is substituted with serine (Ser), and simultaneously, methionine (Met) present at position 234 is substituted with isoleucine (Ile). The allulose epimerase variant W29K/A77S/G216S/M234I according to the present invention has a higher conversion activity of fructose to allulose than the wild-type D-allulose 3-epimerase derived from *Flavonifractor plautii* or its variant W29K/G216S/M234I and has excellent thermal stability especially under high temperature conditions of 60° C. or higher. The D-allulose 3-epimerase variant W29K/G216S/M234I consists of an amino acid sequence represented by SEQ ID NO: 3, in which tryptophan (Trp) present at position 29 is substituted with lysine (Lys), glycine (Gly) present at position 216 is substituted with serine (Ser), and simultaneously methionine (Met) present at position 234 is substituted with isoleucine (Ile) in the amino acid sequence (SEQ ID NO: 1) of wild-type D-allulose 3-epimerase derived from *Flavonifractor plautii*, and in Korean Patent Publication No. 10-2021-0132405, there are disclosed a production method and characteristics. The allulose epimerase variant W29K/A77S/G216S/M234I may be obtained by a method of performing PCR using a polynucleotide (consisting of a nucleotide sequence represented by SEQ ID NO: 4) encoding wild-type D-allulose 3-epimerase variant W29K/G216S/M234I derived from *Flavonifractor plautii* as a template and an oligonucleotide having a predetermined nucleotide sequence as a primer pair, performing overlap extension PCR using a pair of amplified variant fragments as a template and an oligonucleotide introduced with a sequence of a restriction enzyme recognition site as a primer, preparing a recombinant expression vector by inserting a polynucleotide fragment encoding an amino acid sequence of an allulose epimerase variant into an expression vector, preparing a recombinant strain by transforming a host strain with the recombinant expression vector, and then culturing and expressing the recombinant strain. In addition, the polynucleotide (consisting of a nucleotide sequence represented by SEQ ID NO: 4) encoding the D-allulose 3-epimerase variant W29K/G216S/M234I may be prepared by performing PCR using a polynucleotide (consisting of a nucleotide sequence represented by SEQ ID NO: 2) encoding wild-type D-allulose 3-epimerase derived from *Flavonifractor plautii* as a template and an oligonucleotide having a predetermined nucleotide sequence as a primer pair and performing overlap extension PCR using a pair of amplified variant fragments as a template and an oligonucleotide introduced with a sequence of a restriction enzyme recognition site as a primer. The allulose epimerase variant W29K/A77S/G216S/M234I according to the present invention consists of an amino acid sequence represented by SEQ ID NO: 5, but an equivalent range of the allulose epimerase variant W29K/A77S/G216S/M234I according to the present invention is not necessarily limited thereto. For example, in the equivalent range of the allulose epimerase variant W29K/A77S/G216S/M234I according to the present invention, as long as the activity of converting fructose to allulose and thermal stability at high temperature of 60° C. or higher are maintained, some amino acids in the amino acid sequence represented by SEQ ID NO: 5 may be substituted, inserted, and/or deleted. The substitution of the amino acid is preferably performed by conservative amino acid replacement in which the properties of proteins are not changed. In addition, modification of the amino acids may be achieved by glycosylation, acetylation, phosphorylation, and the like. In addition, the equivalent range of the allulose epimerase variant W29K/A77S/G216S/M234I according to the present invention may include proteins with increased structural stability against heat, pH, etc. or increased activity for conversion of fructose to allulose by mutation or modification on the amino acid sequence. In addition, the equivalent range of the allulose epimerase variant W29K/A77S/G216S/M234I according to the present invention may include an amino acid sequence having homology of 70% or more, 80% or more, 90% or more, 95% or more, or 99% or more with any one amino acid sequence of the amino acid sequence represented by SEQ ID NO: 5.

Another aspect of the present invention relates to a method for producing a novel allulose epimerase variant W29K/A77S/G216S/M234I or various elements necessary for producing the novel allulose epimerase variant W29K/A77S/G216S/M234I. The various elements necessary for producing the novel allulose epimerase variant W29K/A77S/G216S/M234I include a polynucleotide, a primer pair, a recombinant vector, a recombinant strain, and the like.

The polynucleotide is a polynucleotide encoding an allulose epimerase variant consisting of the amino acid sequence represented by SEQ ID NO: 5, and preferably consists of a nucleotide sequence represented by SEQ ID NO: 9. As used herein, the term "polynucleotide" refers to any non-modified or modified polyribonucleotide (RNA) or polydeoxyribonucleotide (DNA). The polynucleotide includes single- or double-stranded DNA, DNA as a mixture of single- and double-stranded regions, single- and double-stranded RNA, RNA as a mixture of single- and double-stranded regions, or hybrid molecules thereof, but is not limited thereto. In addition, the equivalent range of the polynucleotide encoding the allulose epimerase variant includes a sequence having substantial identity to the nucleotide sequence represented by SEQ ID NO: 9. The substantial identity refers to having sequence homology of any other sequence of 70% or more, 90% or more, or 98% or more with the nucleotide sequence represented by SEQ ID NO: 9 by aligning any other sequence so as to correspond to the nucleotide sequence represented by SEQ ID NO: 9 as much as possible and analyzing the sequence. It will be easily appreciated by those skilled in the art that a polynucleotide encoding an allulose epimerase variant having the same activity within the range having the substantial identity by substituting, adding or deleting one or more nucleotides in the nucleotide sequence of the polynucleotide using a genetic recombination technique and the like known in the art may be prepared. Comparison of such homology may be performed by calculating homology between two or more sequences as a percentage (%) using a commercially available computer program.

In addition, the primer pair is for synthesizing the polynucleotide encoding the allulose epimerase variant consisting of the amino acid sequence represented by SEQ ID NO: 5, and consists of a forward primer and a reverse primer having the following nucleotide sequences when using the polynucleotide (consisting of the nucleotide sequence represented by SEQ ID NO: 4) encoding the D-allulose 3-epimerase variant W29K/G216S/M234I, as a template.

A77S
*Nucleotide sequence of forward primer (5'→3')
AATACGACCTGAGCAGCGACGATCCGGCGGTG

*Nucleotide sequence of reverse primer (5'→3')
GATCGTCGCTGCTCAGGTCGTATTTGGCCTCCA In addition, the recombinant vector includes a polynucleotide encoding an allulose epimerase variant consisting of an amino acid sequence represented by SEQ ID NO: 5. The recombinant vector may be provided in the form of inserting the polynucleotide encoding the allulose epimerase variant into a cloning vector or an expression vector using a known standard method. The term "cloning vector" as used herein is defined as a material capable of transporting DNA fragments into a host cell and reproducing the DNA fragments. In the present invention, the cloning vector may further include a polyadenylation signal, a transcription termination sequence, and a multiple cloning site. In this case, the multiple cloning site includes at least one endonuclease restriction site. In addition, the cloning vector may further include a promoter. For example, in the present invention, the polynucleotide encoding the allulose epimerase variant W29K/A77S/G216S/M234I may be located upstream of the polyadenylation signal and the transcription termination sequence. In addition, the term "expression vector" as used herein is defined as a DNA sequence required for transcription and translation of cloned DNA in an appropriate host. In addition, the term "expression vector" as used herein refers to a genetic construct including essential regulatory elements operably linked to an insert such that the insert is expressed when present in a cell of an individual. The expression vector may be prepared and purified using standard recombinant DNA techniques. The type of expression vector is not particularly limited as long as the expression vector functions to express a desired gene and produce a desired protein in various host cells such as prokaryotic and eukaryotic cells, but a vector capable of mass-producing a foreign protein in a form similar to a natural state while having a promoter exhibiting strong activity and strong expression power is preferred. The expression vector preferably includes at least a promoter, a start codon, a gene encoding a desired protein, and a stop codon terminator. In addition, the expression vector may also appropriately include DNA encoding a signal peptide, an additional expression control sequence, untranslated regions on the 5' side and 3' side of a desired gene, a selectable marker region, a replicable unit, or the like. The "promoter" means a minimal sequence sufficient to instruct transcription. In addition, the promoter may include a promoter configuration sufficient to express a regulatable promoter-dependent gene induced by a cell type specific or external signal or agent, and these configurations may be located at the 5' or 3' portion of the gene. The promoter includes both a conservative promoter and an inducible promoter. The promoter sequence may be derived from prokaryotes, eukaryotes or viruses. As used herein, the term "operably linked" refers to the association of polynucleotide sequences on a single polynucleotide so that one function is regulated by another function. For example, when the promoter is capable of controlling expression of a coding sequence (i.e., when the coding sequence is under the transcriptional control of the promoter), the promoter is operably linked to the coding sequence, or when a ribosome binding site is located to promote translation, the ribosome binding site is operably linked to the coding sequence. The coding sequence may be operably linked to a regulatory sequence in either a sense or antisense direction. The recombinant vector according to the present invention is preferably an expression vector.

In addition, the recombinant strain is transformed by the polynucleotide encoding the allulose epimerase variant consisting of the amino acid sequence represented by SEQ ID NO: 5 or transformed by the recombinant vector including the polynucleotide. As used herein, the term "recombinant strain" refers to a cell transformed by introducing a polynucleotide encoding at least one target protein or an expression vector having the polynucleotide into a host cell. Methods for preparing a transformant by introducing the expression vector into the host cell include transient transfection, microinjection, transduction, cell fusion, calcium phosphate precipitation, liposome-mediated transfection, DEAE dextran-mediated transfection, polybrene-mediated transfection, electroporation, electroinjection, chemical treatment methods such as PEG, methods using gene guns, etc., heat shock, and the like, but are not limited thereto. The host cell which may be transformed with the expression vector in the present invention is not particularly limited as long as the host cell is known in the art, such as prokaryotic cells, plant cells, insect cells, and animal cells, and preferably, a host having high DNA introduction efficiency and high expression efficiency of the introduced DNA is usually used. For example, the host cell may be *E. coli*. The *E. coli* includes BL21, JM109, K-12, LE392, RR1, DH5α, W3110, or the like, but is not limited thereto. In addition, the host cell may use a strain selected from the group consisting of *Bacillus* strains such as *Bacillus subtilis* and *Bacillus thuringiensis, Corynebacterium* strains such as *Corynebacterium glutamicum, Salmonella* strains such as *Salmonella typhimurium*, and other intestinal bacteria and strains such as *Serratia marcescens* and various *Pseudomonas* species.

In addition, the method for producing the allulose epimerase variant W29K/A77S/G216S/M234I includes expressing the allulose epimerase variant by culturing the recombinant strain transformed by the polynucleotide encoding the allulose epimerase variant consisting of the amino acid sequence represented by SEQ ID NO: 5 or transformed by the recombinant vector including the polynucleotide; and isolating psicose epimerase from a lysate of the recombinant strain in which the allulose epimerase variant is expressed. The protein expression by the host cell may be induced using lactose, isopropyl-1-thio-β-D-galactopyranoside (IPTG) as an inducing factor, etc., and the induction time may be adjusted such that the amount of protein is maximized. In the present invention, the allulose epimerase variant may be recovered from the lysate of the recombinant strain. Cells used for protein expression may be destructed by various physical or chemical means such as repeated freeze-thaw, sonication, mechanical destruction or cell disintegrant, and can be isolated or purified by conventional biochemical isolation techniques (Sambrook et al., Molecular Cloning: A laboratory Manual, 2nd Ed., Cold Spring Harbor Laboratory Press, 1989; Deuscher, M., Guide to Protein Purification Methods Enzymology, Vol. 182. Academic Press. Inc., San Diego, CA, 1990). For example, methods for isolating or purifying proteins expressed by a host cell include electrophoresis, centrifugation, gel filtration, precipitation, dialysis, chromatography (ion exchange chromatography, affinity chromatography, immunosorbent affinity chromatography, reversed phase HPLC, gel permeation HPLC), isoelectric focus and various variations or combination methods thereof, but are not limited thereto. Meanwhile, in the present invention, the step of isolating the allulose epimerase variant from the lysate of the recombinant strain may be preferably performed by affinity chromatography using a peptide tag. The peptide tag may use various known tags such as HA tag, FLAG tag, His tag, biotin carboxyl carrier protein (BCCP), c-myc tag, V5 tag, glutathione-S-transferase (GST), or maltose binding protein (MBP), preferably His tag. His-tagged proteins are specifically trapped on a column of nickel-nitrilotriacetic acid (Ni-NTA) resin and may be eluted with EDTA or imidazole.

Yet another aspect of the present invention relates to a method for producing allulose from fructose or various elements necessary for producing allulose from fructose. The various elements necessary for producing allulose from fructose include a composition for producing allulose.

An example of the composition for producing allulose includes an allulose epimerase variant W29K/A77S/G216S/M234I consisting of an amino acid sequence represented by SEQ ID NO: 5. In addition, another example of the composition for producing allulose includes a recombinant strain transformed by a polynucleotide encoding an allulose epimerase variant consisting of an amino acid sequence represented by SEQ ID NO: 5 or a recombinant vector including the polynucleotide, a culture of the recombinant strain or a lysate of the recombinant strain. In this case, the composition for producing allulose may preferably further include at least one selected from the group consisting of manganese ions, nickel ions, and cobalt ions, and more preferably may further include manganese ions or nickel ions. The novel allulose epimerase variant according to the present invention exhibits properties of a metalloenzyme whose activation is controlled by metal ions, and the reaction by the enzyme may be performed in the presence of a specific metal ion such as manganese ion or nickel ion to increase the production yield of allulose.

In addition, an example of the method for producing allulose from fructose includes reacting fructose with a recombinant strain transformed by a polynucleotide encoding an allulose epimerase variant consisting of an amino acid sequence represented by SEQ ID NO: 5 or a recombinant vector including the polynucleotide, a culture of the recombinant strain, a lysate of the recombinant strain, or a composition including at least one thereof. In addition, the method for producing allulose from fructose may further include adding a metal ion, and the type of metal ion is as described above. For example, the metal ion may be added to fructose as a matrix or to a mixture of the enzyme variant and fructose. In addition, as another example, the metal ion may be added to a carrier immobilized with the enzyme variant (before adding fructose), added to a mixture of the carrier immobilized with the enzyme variant and fructose (after adding fructose), or added in the form of a mixture with fructose when fructose is added. In the case of using the recombinant strain, the metal ion may be added to the culture or the culturing may also be performed in a culture medium to which the metal ion is added. In addition, in the method for producing allulose from fructose, the allulose epimerase variant or the recombinant strain is preferably immobilized on a carrier. The carrier may create an environment in which the activity of the immobilized enzyme may be maintained for a long period of time, and may be selected from all known carriers that may be used for enzyme immobilization. For example, sodium alginate may be used as the carrier. Sodium alginate is a natural colloidal polysaccharide that is abundant in the cell wall of seaweed and consists of β-D-mannuronic acid and α-L-guluronic acid and is formed by randomly forming beta-1,4 bonds in terms of the content to stably immobilize the strain or enzyme and may be advantageous in terms of allulose yield. For example, in order to further improve the yield of allulose, a sodium alginate solution (e.g., sodium alginate aqueous solution) at a concentration of 1.5 to 4.0% (w/v), preferably a sodium alginate solution at a concentration of about 2.5% (w/v) may be used for immobilization of the recombinant strain. In addition, in the method for producing allulose from fructose, the reaction temperature is in the range of 60 to 70° C., preferably 60 to 67° C., and more preferably 60 to 65° C. when considering the stability and maximum activity of the enzyme variant, and the reaction pH is in the range of 6.5 to 8, preferably 6.5 to 7.5, and more preferably 6.5 to 7. In addition, in the method for producing allulose from fructose, the concentration of fructose is not particularly limited, but it is preferably 1 to 75% (w/w), more preferably 4 to 35% (w/w) based on the total reactant in consideration of productivity and economy. In addition, the concentration of the enzyme variant used in the method for producing allulose from fructose may be 0.001 to 0.5 mg/ml, preferably 0.01 to 0.2 mg/ml, and more preferably 0.02 to 0.1 mg/ml based on the total reactant. In addition, when producing allulose from fructose using the recombinant strain, a host strain of the recombinant strain is preferably a food-safe strain. The food-safe strain refers to a generally accepted as safe (GRAS)-class strain that is generally accepted as safe, and may be selected from, for example, *Saccharomyces* sp., *Bacillus* sp., *Corynebacterium* sp., and the like. The strains are industrial microorganisms that produce chemicals having various uses in fields such as feed, medicine, and food. These strains are strains that are easy to genetic manipulation and mass culture, or have high stability under various process conditions. In addition, since these strains have a relatively rigid cell membrane structure compared to other bacteria, these strains exhibit biological characteristics in which the cells exist in a stable state even under the influence of osmotic pressure due to high sugar concentration. Specific examples of the GRAS-class strain include *Saccharomyces cerevisiae*, *Bacillus subtilis*, *Corynebacterium glutamicum*, and the like.

Hereinafter, the present invention will be described in more detail with reference to Examples. However, the following Examples are only for clearly illustrating the technical features of the present invention, but do not limit the protection scope of the present invention.

Example 1: Additional Search for Amino Acid Substitution Sites to Improve Conversion Rate and Thermal Stability of D-Allulose 3-Epimerase The present applicants have previously filed a novel D-allulose epimerase variant W29K/G216S/M234I in which tryptophan (Trp) present at position 29 was substituted with lysine (Lys), glycine (Gly) present at position 216 was substituted with serine (Ser), and simultaneously methionine (Met) present at position 234 was substituted with isoleucine (Ile) in an amino acid sequence of wild-type D-allulose 3-epimerase to improve the conversion rate of fructose to allulose and thermal stability of wild-type D-allulose 3-epimerase derived from *Flavonifractor plautii* [Korean Patent Publication No. 10-2021-0132405 (Nov. 4, 2021)]. The wild-type D-allulose 3-epimerase derived from *Flavonifractor plautii* consisted of an amino acid sequence represented by SEQ ID NO: 1, and a polynucleotide fragment encoding the wild-type D-allulose 3-epimerase consisted of a nucleotide sequence represented by SEQ ID NO: 2. In addition, the D-allulose epimerase variant W29K/G216S/M234I consisted of an amino acid sequence represented by SEQ ID NO: 3, and the polynucleotide fragment encoding the amino acid sequence of the D-allulose epimerase variant W29K/G216S/M234I consisted of a nucleotide sequence represented by SEQ ID NO: 4.

The present inventors predicted a protein structure using a homology modeling technique and searched for an amino acid substitution site based on the amino acid sequence of the D-allulose epimerase variant W29K/G216S/M234I to improve the conversion rate of fructose to allulose and thermal stability of the D-allulose epimerase variant W29K/ G216S/M234I. The homology modeling was performed using a Robetta server, and the prediction and analysis of the protein structure were performed using software programs such as Coot, PyMol, and UCSF Chimera. A total of four amino acid residue positions expected to be related to the improvement of conversion rate and thermal stability when chemical bonds were changed and amino acid residues to be substituted at the positions were selected through three-dimensional structural model analysis of the D-allulose epimerase variant W29K/G216S/M234I.

FIG. 1 shows a total of four amino acid residue positions selected as substitution candidates to improve a conversion rate of fructose to allulose and thermal stability of a D-allulose epimerase variant W29K/G216S/M234I by the present inventors. In FIG. 1, "A77" represents alanine (Als) present at position 77 of the amino acid sequence represented by SEQ ID NO: 3, "E173" represents glutamic acid (Glu) present at position 173 in the amino acid sequence represented by SEQ ID NO: 3, "W209" represents tryptophan (Trp) present at position 209 in the amino acid sequence represented by SEQ ID NO: 3, and "Q240" represents glutamine (Gln) present at position 240 in the amino acid sequence represented by SEQ ID NO: 3.

In addition, as described below, an enzyme variant W29K/A77S/G216S/M234I consisting of an amino acid sequence represented by SEQ ID NO: 5 was prepared by substituting alanine (Als) present at position 77 of the amino acid sequence represented by SEQ ID NO: 3 with serine (Ser), an enzyme variant W29K/E173A/G216S/M234I consisting of an amino acid sequence represented by SEQ ID NO: 6 was prepared by substituting glutamic acid (Glu) present at position 173 of the amino acid sequence represented by SEQ ID NO: 3 with alanine (Ala), an enzyme variant W29K/W209L/G216S/M234I consisting of an amino acid sequence represented by SEQ ID NO: 7 was prepared by substituting tryptophan (Trp) present at position 209 of the amino acid sequence represented by SEQ ID NO: 3 with leucine (Leu), and an enzyme variant W29K/G216S/M234I/Q240D consisting of an amino acid sequence repre-sented by SEQ ID NO: 8 was prepared by substituting glutamine (Gln) present at position 240 of the amino acid sequence represented by SEQ ID NO: 3 with aspartic acid (Asp).

Example 2: Preparation of Recombinant Vector and Recombinant Strain for Overexpression of D-Allulose 3-Epimerase Variant Derived from *Flavonifractor plautii*

Based on the polynucleotide (SEQ ID NO: 4) of the D-allulose epimerase variant W29K/G216S/M234I, polynucleotide fragments encoding amino acid sequences of four enzyme variants W29K/A77S/G216S/M234I, W29K/E173A/G216S/M234I, W29K/W209L/G216S/M234I, and W29K/G216S/M234I/Q240D were prepared using an overlap extension polymerase chain reaction method.

First, a PCR reaction was performed using primers shown in Table 1 below to prepare a gene encoding an allulose epimerase variant derived from *Flavonifractor plautii*. Specifically, in a reaction solution to which 100 μM of deoxynucleotide triphosphates dATP, dCTP, dGTP, and dTTP, 1 pM of oligonucleotide, which was a primer in Table 1, and 100 ng of a polynucleotide (SEQ ID NO: 4) of the D-allulose epimerase variant W29K/G216S/M234I used as a template were mixed, and a PCR reaction was performed at 25 to 30 cycles in the presence of 1 unit of a pfu-X DNA polymerase mixture (Bioneer) using a thermocycler (TP600, TAKARA BIO Inc., JAPAN).

TABLE 1

| Description of primer | Nucleotide sequence of primer (5'→3') |
|---|---|
| A77S forward primer | AATACGACCTGAGCAGCGACGATCCGGCGGTG |
| A77S reverse primer | GATCGTCGCTGCTCAGGTCGTATTTGGCCTCCA |
| E173A forward primer | AAGAGGGCGTGGCGTTTGTCAAGCGCCTGGGC |
| E173A reverse primer | CGCTTGACAAACGCCACGCCCTCTTTGGCGGT |
| W209L forward primer | AGGCGGGCCCCCTGCTGGGGCATTTCCACGTG |
| W209L reverse primer | AATGCCCCAGCAGGGGGCCCGCCTCCAGAATG |
| Q240D forward primer | GCCGCCCTCAAGGATGTGAACTACCAGGGGCC |
| Q240D reverse primer | CTGGTAGTTCACATCCTTGAGGGCGGCGGCAAT |

After amplifying the variant fragments through primer combination, polynucleotide fragments encoding amino acid sequences of four enzyme variants W29K/A77S/G216S/M234I, W29K/E173A/G216S/M234I, W29K/W209L/G216S/M234I, and W29K/G216S/M234I/Q240D were finally prepared using each pair as a template and an oligonucleotide into which sequences of NdeI and XhoI restriction enzyme recognition sites were introduced as primers, through overlap extension PCR. Table 2 below showed the nucleotide sequences of primers used to introduce the sequences of the restriction enzyme recognition sites.

TABLE 2

| Description of primer | Nucleotide sequence of primer (5'→3') |
|---|---|
| NdeI forward primer | GCATGCCATATGAACCCGATTGGAATGCA |
| XhoI reverse primer | GCATGCCTCGAGCGCGGTCAGCTCCTTGAGGA |

The nucleotide sequence represented by SEQ ID NO: 9 represented a polynucleotide fragment encoding the amino acid sequence of the enzyme variant W29K/A77S/G216S/M234I, the nucleotide sequence represented by SEQ ID NO: 10 represented a polynucleotide fragment encoding the amino acid sequence of the enzyme variant W29K/E173A/G216S/M234I, the nucleotide sequence represented by SEQ ID NO: 11 represented a polynucleotide fragment encoding the amino acid sequence of the enzyme variant W29K/W209L/G216S/M234I, and the nucleotide sequence represented by SEQ ID NO: 12 represented a polynucleotide fragment encoding the amino acid sequence of the enzyme variant W29K/G216S/M234I/Q240D. The nucleotide sequences represented by SEQ ID NOs: 9 to 12 consisted of nucleotide sequences directly corresponding to the amino acid sequences of the enzyme variants, and the sequences of the restriction enzyme recognition sites were omitted for convenience.

Thereafter, the prepared polynucleotide fragments were inserted into the same restriction enzyme site of an expression vector pET28a (Novagen), using the restriction enzymes NdeI and XhoI to prepare four recombinant expression vectors. In addition, the recombinant expression vectors were introduced and transformed into *E. coli* BL21(DE3) (Invitrogen) using a heat shock method (see Sambrook and Russell: Molecular Cloning.) to prepare four types of recombinant *E. coli*. A 60% glycerin solution was added to the prepared recombinant *E. coli*, and frozen-stored at −70° C. before culture for enzyme expression.

Example 3: Expression and Purification of D-Allulose 3-Epimerase Variants Derived from *Flavonifractor plautii*

1 ml of the recombinant *E. coli* prepared in Example 2 was inoculated in a 1 L flask containing 150 ml of a protein expression medium having a composition (based on 1 L of medium) of Table 3 below, and cultured in a shaking incubator for 24 hr while maintaining a temperature condition of 32° C. and a shaking condition of 140 rpm. Overexpression of the allulose epimerase variant was induced with 1% lactose contained in the medium.

TABLE 3

| Medium component | Content | Medium component | Content |
|---|---|---|---|
| Glycerol | 9.0 wt % | $MgSO_4$ | 0.1 wt % |
| Lactose | 1.0 wt % | $FeSO_4$ | 10.0 ppm |
| $(NH_4)_2SO_4$ | 0.6 wt % | $MnSO_4$ | 10.0 ppm |
| $KH_2PO_4$ | 0.5 wt % | $ZnSO_4$ | 10.0 ppm |
| YPA | 1.5 wt % | Defoamer (Neorin) | 1.0 drop |

Thereafter, the overexpressed allulose epimerase variant was isolated by the following method. First, the culture medium of the recombinant *E. coli* was centrifuged for about 15 minutes at 4100×g and 4° C. to remove a supernatant, and the cells of the recombinant *E. coli* were recovered. Thereafter, the recovered cells of the recombinant *E. coli* were suspended in a lysis buffer (containing 50 mM potassium monophosphate, 300 mM potassium chloride, and 5 mM imidazole), and then treated with a sonicator to lyze the cells. Thereafter, the cell lysate was centrifuged at 15,814×g and 4° C. for about 10 minutes to remove a cell pellet, and only the supernatant was recovered. Thereafter, a purified enzyme solution containing the allulose epimerase variant was isolated from the recovered supernatant using a His-tag affinity chromatography column and a desalting column.

Example 4: Confirmation of Conversion Rate of Fructose to Allulose and Thermal Stability of D-Allulose 3-Epimerase Variants In order to confirm the conversion rate of fructose to allulose and thermal stability of the D-allulose epimerase variant W29K/G216S/M234I [Korean Patent Publication No. 10-2021-0132405 (Nov. 4, 2021)] previously filed by the present applicants and four D-allulose epimerase variants W29K/A77S/G216S/M234I, W29K/E173A/G216S/M234I, W29K/VV209L/G216S/M234I, and W29K/G216S/M234I/Q240D newly prepared in the present invention, the enzyme was exposed to a high temperature for a predetermined time, and then the degree of reduction in the conversion activity of fructose to allulose was analyzed. Specifically, the W29K/G216S/M234I purified enzyme solution obtained in Example 3 of Korean Patent Publication No. 10-2021-0132405 (Nov. 4, 2021) (enzyme concentration of 0.3 mg/ml) and the purified enzyme solution (enzyme concentration of 0.3 mg/ml) obtained in Example 3 of the present invention were stored in a constant temperature water bath at 62° C. for 0 hr, 0.5 hr, 1 hr, 1.5 hr, and 2 hr, and then heat-treated. Thereafter, the heat-treated purified enzyme solution was added to a 50 mM PIPES buffer (pH 7.0) containing 10% (w/w) fructose and metal ions of 1 mM manganese sulfate ($MnSO_4$) so that the enzyme concentration was 75 µg/ml and reacted for 10 minutes under a temperature condition of 62° C. and a shaking condition of 120 rpm using a shaking constant temperature water bath (VS-1205SW1, vision science). Thereafter, the reaction was stopped by lowering the temperature of the reaction product to 4° C., and the supernatant was recovered by centrifugation under conditions of 16,600×g and 4° C. Thereafter, the concentration of allulose and the concentration of fructose in the supernatant were measured using a high-performance liquid chromatography (HPLC) system (SP930D pump, Younglin Instruments; MIDAS auto injector, Spark Holland Co.) equipped with a sugar analysis column (Benson, USA) and a refractive index detector (2414 refractive index detector, Waters Co.), the conversion rate of fructose to allulose was calculated from the measured result, and then the conversion rate was used as an index of enzyme activity.

Table 4 below showed the conversion rate of fructose to allulose for each heat treatment condition when D-allulose 3-epimerase variants derived from *Flavonifractor plautii* were heat-treated.

TABLE 4

Conversion rate (%) of fructose to allulose by heat treatment time of allulose epimerase variants

| Heat treatment time at 62° C. | W29K/ G216G/ M234I | W29K/ A77S/ G216S/ M234I | W29K/ E173A/ G216S/ M234I | W29K/ W209L/ G216S/ M234I | W29K/ G216S/ M234I/ Q240D |
|---|---|---|---|---|---|
| 0 hr | 9.88 | 9.86 | 9.08 | 9.47 | 8.78 |
| 0.5 hr | 6.59 | 7.31 | 5.73 | 6.29 | 6.01 |
| 1 hr | 5.69 | 6.09 | 4.55 | 5.44 | 5.01 |
| 1.5 hr | 4.50 | 4.88 | 3.66 | 4.38 | 4.15 |
| 2 hr | 4.06 | 4.33 | 3.32 | 3.92 | 3.70 |

As shown in Table 4 above, most of the D-allulose 3-epimerase variants derived from *Flavonifractor plautii* newly prepared based on the amino acid sequence of the D-allulose 3-epimerase variant W29K/G216S/M234I derived from *Flavonifractor plautii* had lower conversion activity of fructose to allulose and thermal stability than those of W29K/G216S/M234I. On the other hand, the D-allulose 3-epimerase variant W29K/A77S/G216S/M234I had the conversion activity of fructose to allulose similar to or higher than the D-allulose 3-epimerase variant W29K/G216S/M234I regardless of the heat treatment time, and especially showed remarkably improved thermal stability.

As described above, the present invention has been described through Examples above, but the present invention is not necessarily limited thereto, and various modifications can be made without departing from the scope and spirit of the present invention. Therefore, the scope of the present invention should be construed to include all embodiments falling within the scope of claims appended hereto.

The invention claimed is:

1. An allulose epimerase variant consisting of an amino acid sequence represented by SEQ ID NO: 5.

2. A polynucleotide encoding the allulose epimerase variant of claim 1.

3. The polynucleotide of claim 2, wherein the polynucleotide consists of a nucleotide sequence represented by SEQ ID NO: 9.

4. A recombinant vector comprising the polynucleotide of claim 2.

5. A recombinant strain transformed by the polynucleotide of claim 2.

6. A method for producing an allulose epimerase variant comprising:
   expressing an allulose epimerase variant by culturing the recombinant strain of claim 5; and
   isolating the allulose epimerase variant from a lysate of the recombinant strain in which the allulose epimerase variant is expressed.

7. A composition for producing allulose comprising the allulose epimerase variant of claim 1.

8. A composition for producing allulose comprising the recombinant strain of claim 5, a culture of the recombinant strain or a lysate of the recombinant strain.

9. A method for producing allulose comprising reacting fructose with the allulose epimerase variant of claim 1 or a composition including the allulose epimerase variant.

10. A method for producing allulose comprising reacting fructose with the recombinant strain of claim 5, a culture of the recombinant strain, a lysate of the recombinant strain, or a composition including at least one thereof.

11. A recombinant strain transformed by the polynucleotide of claim 3.

12. A recombinant strain transformed by the recombinant vector of claim 4.

* * * * *

SEQUENCE LISTING

```
<160> NUMBER OF SEQ ID NOS: 22

<210> SEQ ID NO 1
<211> LENGTH: 294
<212> TYPE: PRT
<213> ORGANISM: Unknown
<220> FEATURE:
<223> OTHER INFORMATION: Wild type D-allulose 3-epimerase derived from
      Flavonifractor plautii

<400> SEQUENCE: 1

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Trp Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Gly Glu Asn Asn Arg Arg Pro Ala Gly
    210                 215                 220

Ser Thr Asn Arg Leu Pro Trp Lys Asp Met Ala Ala Ala Leu Lys Gln
225                 230                 235                 240
```

```
Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
        290
```

<210> SEQ ID NO 2
<211> LENGTH: 885
<212> TYPE: DNA
<213> ORGANISM: Unknown
<220> FEATURE:
<223> OTHER INFORMATION: Polynucleotide coding wild type D-allulose
      3-epimerase derived from Flavonifractor plautii

<400> SEQUENCE: 2

```
atgaacccga ttggaatgca ctacggcttc tggagccaca actgggacga gattgcatac      60 ataccectga tggagaagct ggcctggctg gctttgaca tctgcgaggt ggcctccgcc     120
gagtggggct attacgacga cgccaggctg cgggagctga aggcctgcgc cgatcacaac     180
ggcctgggca tcacctattc catcggcctg gaggccaaat acgacctggc cagcgacgat     240
ccggcggtgc gggagaacgg catccgccat gtcacccgca tcctggagag catgcccaag     300 gtggggggcgg ccatcctcaa cggcgtgtcc tacgccgggt ggcaggccct gcccgaccac     360
ggaatcaccc tggacgagaa cgccgcaag gaggagcttg ccctggagtc catgtcccgg     420
ctcatgaagg tggcggagga ctgcggcgtg ctctactgct gcgaggtggt caaccgcttc     480
gagcagtacc tgctcaacac cgccaaagag ggcgtggagt tgtcaagcg cctgggcagt     540 cccaacgccc gggtgctgct ggataccttc cacatgaaca tcgaggagga cagcatggtg     600
gacgccattc tggaggcggg ccctggctg gggcatttcc acgtggggga gaacaaccgc     660
cgccccgccg gctccaccaa ccgcctgccc tggaaggaca tggccgccgc cctcaagcag     720
gtgaactacc aggggccat tgtgatggag cccttcgtgc tcatgggggg taccattccc     780
tatgatatca aggtctggcg ggatctcagc ggcggggccg ggaggccgg gctggacgag     840 atggcgggcc gggcctgccg gttcctcaag gagctgaccg cgtaa                      885
```

<210> SEQ ID NO 3
<211> LENGTH: 294
<212> TYPE: PRT
<213> ORGANISM: Artificial Sequence
<220> FEATURE:
<223> OTHER INFORMATION: D-allulose 3-epimerase variant W29K/G216S/M234I

<400> SEQUENCE: 3

```
Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80
```

```
Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220

Ser Thr Asn Arg Leu Pro Trp Lys Asp Ile Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 4
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/G216S/M234

<400> SEQUENCE: 4
atgaacccga ttggaatgca ctacggcttc tggagccaca actgggacga gattgcatac      60 ataccctga  tggagaagct ggccaaactg gctttgaca  tctgcgaggt ggcctccgcc     120
gagtggggct attacgacga cgccaggctg cgggagctga aggcctgcgc cgatcacaac     180
ggcctgggca tcacctattc catcggcctg gaggccaaat acgacctggc cagcgacgat     240
ccggcggtgc gggagaacgg catccgccat gtcacccgca tcctggagag catgcccaag     300
gtgggggcgg ccatcctcaa cggcgtgtcc tacgccgggt ggcaggccct gcccgaccac     360
ggaatcaccc tggacgagaa gcgccgcaag gaggagcttg ccctggagtc catgtcccgg     420
ctcatgaagg tggcggagga ctgcggcgtg ctctactgct gcgaggtggt caaccgcttc     480
gagcagtacc tgctcaacac cgccaaagag ggcgtggagt ttgtcaagcg cctgggcagt     540
cccaacgccc gggtgctgct ggatacattc cacatgaaca tcgaggagga cagcatggtg     600
gacgccattc tggaggcggg ccctggctg  ggcattttcc acgtgagcga gaacaaccgc     660
cgccccgccg gctccaccaa ccgcctgccc tggaaggaca ttgccgccgc cctcaagcag     720
gtgaactacc aggggggccat tgtgatggag cccttcgtgc tcatggggggg taccattccc     780
```

```
tatgatatca aggtctggcg ggatctcagc ggcggggccg gggaggccgg gctggacgag    840
atggcgggcc gggcctgccg gttcctcaag gagctgaccg cgtaa                   885
```

```
<210> SEQ ID NO 5
<211> LENGTH: 294
<212> TYPE: PRT
<213> ORGANISM: Artificial Sequence
<220> FEATURE:
<223> OTHER INFORMATION: D-allulose 3-epimerase variant
      W29K/A77S/G216S/M234I

<400> SEQUENCE: 5
```

| | | | | | | | | | | | | | | |
|---|---|---|---|---|---|---|---|---|---|---|---|---|---|---|
| Met | Asn | Pro | Ile | Gly | Met | His | Tyr | Gly | Phe | Trp | Ser | His | Asn | Trp | Asp |
| 1 | | | | 5 | | | | | 10 | | | | | 15 | |

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
                20                  25                  30

Asp Ile Cys Glu Val Ala Ser Ala Glu Trp Gly Tyr Tyr Asp Asp Ala
            35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ser Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220

Ser Thr Asn Arg Leu Pro Trp Lys Asp Ile Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

```
<210> SEQ ID NO 6
<211> LENGTH: 294
<212> TYPE: PRT
<213> ORGANISM: Artificial Sequence
<220> FEATURE:
<223> OTHER INFORMATION: D-allulose 3-epimerase variant
```

W29K/E173A/G216S/M234I

<400> SEQUENCE: 6

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala
        35                  40                  45

Arg Leu Arg Glu Leu Lys Ala Cys Ala Asp His Asn Gly Leu Gly Ile
    50                  55                  60

Thr Tyr Ser Ile Gly Leu Glu Ala Lys Tyr Asp Leu Ala Ser Asp Asp
65                  70                  75                  80

Pro Ala Val Arg Glu Asn Gly Ile Arg His Val Thr Arg Ile Leu Glu
                85                  90                  95

Ser Met Pro Lys Val Gly Ala Ala Ile Leu Asn Gly Val Ser Tyr Ala
            100                 105                 110

Gly Trp Gln Ala Leu Pro Asp His Gly Ile Thr Leu Asp Glu Lys Arg
        115                 120                 125

Arg Lys Glu Glu Leu Ala Leu Glu Ser Met Ser Arg Leu Met Lys Val
    130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Ala Phe Val Lys
                165                 170                 175

Arg Leu Gly Ser Pro Asn Ala Arg Val Leu Leu Asp Thr Phe His Met
            180                 185                 190

Asn Ile Glu Glu Asp Ser Met Val Asp Ala Ile Leu Glu Ala Gly Pro
        195                 200                 205

Trp Leu Gly His Phe His Val Ser Glu Asn Asn Arg Arg Pro Ala Gly
    210                 215                 220

Ser Thr Asn Arg Leu Pro Trp Lys Asp Ile Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
            260                 265                 270

Ala Gly Glu Ala Gly Leu Asp Glu Met Ala Gly Arg Ala Cys Arg Phe
        275                 280                 285

Leu Lys Glu Leu Thr Ala
    290

<210> SEQ ID NO 7
<211> LENGTH: 294
<212> TYPE: PRT
<213> ORGANISM: Artificial Sequence
<220> FEATURE:
<223> OTHER INFORMATION: D-allulose 3-epimerase variant
      W29K/W209L/G216S/M234I

<400> SEQUENCE: 7

Met Asn Pro Ile Gly Met His Tyr Gly Phe Trp Ser His Asn Trp Asp
1               5                   10                  15

Glu Ile Ala Tyr Ile Pro Leu Met Glu Lys Leu Ala Lys Leu Gly Phe
            20                  25                  30

Asp Ile Cys Glu Val Ala Ser Ala Glu Trp Gly Tyr Tyr Asp Asp Ala

```
            35                  40                  45
Arg Leu Arg Glu Leu Lys Ala Cys Ala Asp His Asn Gly Leu Gly Ile
 50                  55                  60

Thr Tyr Ser Ile Gly Leu Glu Ala Lys Tyr Asp Leu Ala Ser Asp Asp
 65                  70                  75                  80

Pro Ala Val Arg Glu Asn Gly Ile Arg His Val Thr Arg Ile Leu Glu
                 85                  90                  95

Ser Met Pro Lys Val Gly Ala Ala Ile Leu Asn Gly Val Ser Tyr Ala
                100                 105                 110

Gly Trp Gln Ala Leu Pro Asp His Gly Ile Thr Leu Asp Glu Lys Arg
            115                 120                 125

Arg Lys Glu Glu Leu Ala Leu Glu Ser Met Ser Arg Leu Met Lys Val
130                 135                 140

Ala Glu Asp Cys Gly Val Leu Tyr Cys Cys Glu Val Val Asn Arg Phe
145                 150                 155                 160

Glu Gln Tyr Leu Leu Asn Thr Ala Lys Glu Gly Val Glu Phe Val Lys
                165                 170                 175

Arg Leu Gly Ser Pro Asn Ala Arg Val Leu Leu Asp Thr Phe His Met
                180                 185                 190

Asn Ile Glu Glu Asp Ser Met Val Asp Ala Ile Leu Glu Ala Gly Pro
            195                 200                 205

Leu Leu Gly His Phe His Val Ser Glu Asn Asn Arg Arg Pro Ala Gly
210                 215                 220

Ser Thr Asn Arg Leu Pro Trp Lys Asp Ile Ala Ala Ala Leu Lys Gln
225                 230                 235                 240

Val Asn Tyr Gln Gly Ala Ile Val Met Glu Pro Phe Val Leu Met Gly
                245                 250                 255

Gly Thr Ile Pro Tyr Asp Ile Lys Val Trp Arg Asp Leu Ser Gly Gly
                260                 265                 270

Ala Gly Glu Ala Gly Leu Asp Glu Met Ala Gly Arg Ala Cys Arg Phe
            275                 280                 285

Leu Lys Glu Leu Thr Ala
    290

<210> SEQ ID NO 8
<211> LENGTH: 294
<212> TYPE: PRT
<213> ORGANISM: Artificial Sequence
<220> FEATURE:
<223> OTHER INFORMATION: D-allulose 3-epimerase variant
      W29K/G216S/M234I/Q240D

<400> SEQUENCE: 8

Met Asn Pro Ile Gly Met His Tyr Gly Phe Trp Ser His Asn Trp Asp
 1               5                  10                  15

Glu Ile Ala Tyr Ile Pro Leu Met Glu Lys Leu Ala Lys Leu Gly Phe
                20                  25                  30

Asp Ile Cys Glu Val Ala Ser Ala Glu Trp Gly Tyr Tyr Asp Asp Ala
            35                  40                  45

Arg Leu Arg Glu Leu Lys Ala Cys Ala Asp His Asn Gly Leu Gly Ile
 50                  55                  60

Thr Tyr Ser Ile Gly Leu Glu Ala Lys Tyr Asp Leu Ala Ser Asp Asp
 65                  70                  75                  80

Pro Ala Val Arg Glu Asn Gly Ile Arg His Val Thr Arg Ile Leu Glu
                 85                  90                  95
```

```
Ser Met Pro Lys Val Gly Ala Ala Ile Leu Asn Gly Val Ser Tyr Ala
            100                 105                 110
Gly Trp Gln Ala Leu Pro Asp His Gly Ile Thr Leu Asp Glu Lys Arg
        115                 120                 125
Arg Lys Glu Glu Leu Ala Leu Glu Ser Met Ser Arg Leu Met Lys Val
    130                 135                 140
Ala Glu Asp Cys Gly Val Leu Tyr Cys Cys Glu Val Val Asn Arg Phe
145                 150                 155                 160
Glu Gln Tyr Leu Leu Asn Thr Ala Lys Glu Gly Val Glu Phe Val Lys
                165                 170                 175
Arg Leu Gly Ser Pro Asn Ala Arg Val Leu Leu Asp Thr Phe His Met
            180                 185                 190
Asn Ile Glu Glu Asp Ser Met Val Asp Ala Ile Leu Glu Ala Gly Pro
        195                 200                 205
Trp Leu Gly His Phe His Val Ser Glu Asn Asn Arg Arg Pro Ala Gly
    210                 215                 220
Ser Thr Asn Arg Leu Pro Trp Lys Asp Ile Ala Ala Ala Leu Lys Asp
225                 230                 235                 240
Val Asn Tyr Gln Gly Ala Ile Val Met Glu Pro Phe Val Leu Met Gly
                245                 250                 255
Gly Thr Ile Pro Tyr Asp Ile Lys Val Trp Arg Asp Leu Ser Gly Gly
            260                 265                 270
Ala Gly Glu Ala Gly Leu Asp Glu Met Ala Gly Arg Ala Cys Arg Phe
        275                 280                 285
Leu Lys Glu Leu Thr Ala
    290

<210> SEQ ID NO 9
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/A77S/G216S/M234I

<400> SEQUENCE: 9
atgaacccga ttggaatgca ctacggcttc tggagccaca actgggacga gattgcatac      60
atacccctga tggagaagct ggccaaactg gcctttgaca tctgcgaggt ggcctccgcc     120
gagtggggct attacgacga cgccaggctg cgggagctga aggcctgcgc cgatcacaac     180
ggcctgggca tcacctattc catcggcctg gaggccaaat acgacctgag cagcgacgat     240
ccggcggtgc gggagaacgg catccgccat gtcacccgca tcctggagag catgcccaag     300 gtggggcgg ccatcctcaa cggcgtgtcc tacgccgggt ggcaggccct gcccgaccac      360
ggaatcaccc tggacgagaa gcgccgcaag gaggagcttg ccctggagtc catgtcccgg     420
ctcatgaagg tggcggagga ctgcggcgtg ctctactgct gcgaggtggt caaccgcttc     480
gagcagtacc tgctcaacac cgccaaagag ggcgtggagt ttgtcaagcg cctgggcagt     540
cccaacgccc gggtgctgct ggataccttc acatgaaca tcgaggagga cagcatggtg      600
gacgccattc tggaggcggg ccctggctg gggcatttcc acgtgagcga gaacaaccgc      660
cgccccgccg gctccaccaa ccgcctgccc tggaaggaca ttgccgccgc cctcaagcag     720
gtgaactacc aggggccat tgtgatggag cccttcgtgc tcatggggg taccattccc       780 tatgatatca aggtctggcg ggatctcagc ggcggggccg gggaggccgg gctggacgag     840
atggcgggcc gggcctgccg gttcctcaag gagctgaccg cgtaa                     885
```

<210> SEQ ID NO 10
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/E173A/G216S/M234I

<400> SEQUENCE: 10

```
atgaacccga ttggaatgca ctacggcttc tggagccaca actgggacga gattgcatac     60
ataccctga tggagaagct ggccaaactg gctttgaca tctgcgaggt ggcctccgcc      120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg     420
ctcatgaagg tggcggagga ctgcggcgtg ctctactgct gcgaggtggt caaccgcttc    480
gagcagtacc tgctcaacac cgccaaagag ggcgtggcgt tgtcaagcg cctgggcagt    540
cccaacgccc gggtgctgct ggatacctcc cacatgaaca tcgaggagga cagcatggtg    600
gacgccattc tggaggcggg ccctggctg gggcatttcc acgtgagcga gaacaaccgc     660
cgccccgccg gctccaccaa ccgcctgccc tggaaggaca ttgccgccgc cctcaagcag    720
gtgaactacc aggggggcat tgtgatggag ccttcgtgc tcatgggggg taccattccc    780
tatgatatca aggtctggcg ggatctcagc ggcggggccg gggaggccgg gctggacgag    840
atggcgggcc gggcctgccg gttcctcaag gagctgaccg cgtaa                   885
```

<210> SEQ ID NO 11
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/W209L/G216S/M234I

<400> SEQUENCE: 11

```
atgaacccga ttggaatgca ctacggcttc tggagccaca actgggacga gattgcatac     60
ataccctga tggagaagct ggccaaactg gctttgaca tctgcgaggt ggcctccgcc      120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300
gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg     420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540
cccaacgccc gggtgctgct ggatacctcc cacatgaaca tcgaggagga cagcatggtg    600
gacgccattc tggaggcggg ccctggctg gggcatttcc acgtgagcga gaacaaccgc     660
cgccccgccg gctccaccaa ccgcctgccc tggaaggaca ttgccgccgc cctcaagcag    720
gtgaactacc aggggggcat tgtgatggag ccttcgtgc tcatgggggg taccattccc    780
```

```
tatgatatca aggtctggcg ggatctcagc ggcggggccg gggaggccgg gctggacgag    840
atggcgggcc gggcctgccg gttcctcaag gagctgaccg cgtaa                   885
```

<210> SEQ ID NO 12
<211> LENGTH: 885
<212> TYPE: DNA
<213> ORGANISM: Artificial Sequence
<220> FEATURE:
<223> OTHER INFORMATION: Polynucleotide coding D-allulose 3-epimerase
      variant W29K/G216S/M234I/Q240D

<400> SEQUENCE: 12

```
atgaacccga ttggaatgca ctacggcttc tggagccaca actgggacga gattgcatac    60 ataccoctga tggagaagct ggccaaactg gctttgaca tctgcgaggt ggcctccgcc    120
gagtggggct attacgacga cgccaggctg cgggagctga aggcctgcgc cgatcacaac    180
ggcctgggca tcacctattc catcggcctg gaggccaaat acgacctggc cagcgacgat    240
ccggcggtgc gggagaacgg catccgccat gtcacccgca tcctggagag catgcccaag    300 gtggggcgg ccatcctcaa cggcgtgtcc tacgccgggt ggcaggccct gcccgaccac    360
ggaatcaccc tggacgagaa cgccgcaag gaggagcttg ccctggagtc catgtcccgg    420
ctcatgaagg tggcggagga ctgcggcgtg ctctactgct gcgaggtggt caaccgcttc    480
gagcagtacc tgctcaacac cgccaaagag ggcgtggagt tgtcaagcg cctgggcagt    540 cccaacgccc gggtgctgct ggataccttc cacatgaaca tcgaggagga cagcatggtg    600
gacgccattc tggaggcggg ccctggctg gggcatttcc acgtgagcga gaacaaccgc    660 cgcccgccg gctccaccaa ccgcctgccc tggaaggaca ttgccgccgc cctcaaggat    720
gtgaactacc aggggccat tgtgatggag cccttcgtgc tcatgggggg taccattccc    780
tatgatatca aggtctggcg ggatctcagc ggcggggccg gggaggccgg gctggacgag    840
atggcgggcc gggcctgccg gttcctcaag gagctgaccg cgtaa                   885
```

<210> SEQ ID NO 13
<211> LENGTH: 32
<212> TYPE: DNA
<213> ORGANISM: Unknown
<220> FEATURE:
<223> OTHER INFORMATION: Forward primer for A77S

<400> SEQUENCE: 13

```
aatacgacct gagcagcgac gatccggcgg tg                                 32
```

<210> SEQ ID NO 14
<211> LENGTH: 33
<212> TYPE: DNA
<213> ORGANISM: Unknown
<220> FEATURE:
<223> OTHER INFORMATION: Reverse primer for A77S

<400> SEQUENCE: 14

```
gatcgtcgct gctcaggtcg tatttggcct cca                                33
```

<210> SEQ ID NO 15
<211> LENGTH: 32
<212> TYPE: DNA
<213> ORGANISM: Unknown
<220> FEATURE:
<223> OTHER INFORMATION: E173A forward primer

<400> SEQUENCE: 15
aagagggcgt ggcgtttgtc aagcgcctgg gc        32

<210> SEQ ID NO 16
<211> LENGTH: 32
<212> TYPE: DNA
<213> ORGANISM: Unknown
<220> FEATURE:
<223> OTHER INFORMATION: E173A reverse primer

<400> SEQUENCE: 16
cgcttgacaa acgccacgcc ctctttggcg gt        32

<210> SEQ ID NO 17
<211> LENGTH: 32
<212> TYPE: DNA
<213> ORGANISM: Unknown
<220> FEATURE:
<223> OTHER INFORMATION: W209L forward primer

<400> SEQUENCE: 17
aggcgggccc cctgctgggg catttccacg tg        32

<210> SEQ ID NO 18
<211> LENGTH: 32
<212> TYPE: DNA
<213> ORGANISM: Unknown
<220> FEATURE:
<223> OTHER INFORMATION: W209L reverse primer

<400> SEQUENCE: 18
aatgccccag caggggggccc gcctccagaa tg        32

<210> SEQ ID NO 19
<211> LENGTH: 33
<212> TYPE: DNA
<213> ORGANISM: Unknown
<220> FEATURE:
<223> OTHER INFORMATION: Q240D forward primer

<400> SEQUENCE: 19
gccgccctca aggatgtgaa ctaccagggg gcc        33

<210> SEQ ID NO 20
<211> LENGTH: 33
<212> TYPE: DNA
<213> ORGANISM: Unknown
<220> FEATURE:
<223> OTHER INFORMATION: Q240D reverse primer

<400> SEQUENCE: 20
ctggtagttc acatccttga gggcggcggc aat        33

<210> SEQ ID NO 21
<211> LENGTH: 29
<212> TYPE: DNA
<213> ORGANISM: Unknown
<220> FEATURE:
<223> OTHER INFORMATION: NdeI forward primer

<400> SEQUENCE: 21
gcatgccata tgaacccgat tggaatgca           29

<210> SEQ ID NO 22
<211> LENGTH: 32
<212> TYPE: DNA
<213> ORGANISM: Unknown

```
<220> FEATURE:
<223> OTHER INFORMATION: NdeI reverse primer

<400> SEQUENCE: 22
gcatgcctcg agcgcggtca gctccttgag ga                                        32
```